United States Patent
Yamamoto et al.

(10) Patent No.: US 11,096,822 B2
(45) Date of Patent: Aug. 24, 2021

(54) OPHTHALMIC DELIVERY DEVICE

(71) Applicant: Oxular Limited, Oxford (GB)

(72) Inventors: Ronald K. Yamamoto, San Francisco, CA (US); Stanley R. Conston, San Carlos, CA (US)

(73) Assignee: Oxular Limited, Oxford (GB)

( * ) Notice: Subject to any disclaimer, the term of this patent is extended or adjusted under 35 U.S.C. 154(b) by 162 days.

(21) Appl. No.: 15/512,130

(22) PCT Filed: Sep. 18, 2015

(86) PCT No.: PCT/EP2015/071520
§ 371 (c)(1),
(2) Date: Mar. 17, 2017

(87) PCT Pub. No.: WO2016/042162
PCT Pub. Date: Mar. 24, 2016

(65) Prior Publication Data
US 2017/0273825 A1    Sep. 28, 2017

Related U.S. Application Data

(60) Provisional application No. 62/052,952, filed on Sep. 19, 2014.

(51) Int. Cl.
*A61F 9/00* (2006.01)
*A61M 5/20* (2006.01)
(Continued)

(52) U.S. Cl.
CPC .......... *A61F 9/0008* (2013.01); *A61M 5/204* (2013.01); *A61F 9/0017* (2013.01);
(Continued)

(58) Field of Classification Search
CPC .... A61F 9/0008; A61F 9/0017; A61F 9/0026; A61F 9/00709; A61M 5/204;
(Continued)

(56) References Cited

U.S. PATENT DOCUMENTS

| | | | |
|---|---|---|---|
| 1,641,976 A | * | 9/1927 | Laurent ................. A61M 5/204 604/184 |
| 3,890,971 A | * | 6/1975 | Leeson ................... A61M 5/24 206/365 |

(Continued)

FOREIGN PATENT DOCUMENTS

| | | |
|---|---|---|
| CN | 103327939 | 9/2013 |
| DE | 102010048085 | 4/2012 |

(Continued)

OTHER PUBLICATIONS

Non-final Office Action dated Aug. 28, 2020 in related U.S. Appl. No. 15/760,717.

(Continued)

*Primary Examiner* — Nilay J Shah
(74) *Attorney, Agent, or Firm* — Stradley Ronon Stevens & Young, LLP

(57) ABSTRACT

Injection device comprising an elongated body (1) with a hollow needle (8) at a distal end; a reservoir for an injection material to be delivered through the needle; a plunger (3) with a first force element (5) configured to provide an injection force to said injection material, and a distal element (10) attached to the distal end of the device thereby sealing a needle lumen, wherein the distal element comprises a tissue interface and a distal seal (11), and wherein the distal seal is penetrable by a distal tip of the needle by the application of pressure on a tissue surface with the distal end of the device, wherein the penetrated distal element becomes slidable on the needle to allow advancement of the needle into tissue, wherein the penetrated distal seal opens a path for flow or delivery of the injection material from the distal end of the needle.

38 Claims, 6 Drawing Sheets

(51) Int. Cl.
*A61M 5/32* (2006.01)
*A61M 5/28* (2006.01)
*A61M 25/00* (2006.01)

(52) U.S. Cl.
CPC ............ *A61M 5/2033* (2013.01); *A61M 5/288* (2013.01); *A61M 25/0084* (2013.01); *A61M 2005/206* (2013.01); *A61M 2005/2013* (2013.01); *A61M 2005/3267* (2013.01); *A61M 2210/0612* (2013.01)

(58) Field of Classification Search
CPC ........ A61M 2005/2013; A61M 5/2033; A61M 5/31591; A61M 5/3243; A61M 5/283; A61M 5/285; A61M 5/286; A61M 2005/2026; A61M 2005/206; A61M 2005/3267; A61M 2005/3128; A61M 2005/3114; A61M 2005/2418; A61M 2210/0612; F16F 1/027
See application file for complete search history.

(56) References Cited

U.S. PATENT DOCUMENTS

| | | | |
|---|---|---|---|
| 5,236,424 A * | 8/1993 | Imran | A61M 25/0074 604/264 |
| 5,250,031 A * | 10/1993 | Kaplan | A61M 5/3275 604/110 |
| 5,295,972 A | 3/1994 | Mischenko | |
| 5,358,489 A * | 10/1994 | Wyrick | A61M 5/002 604/135 |
| 5,665,071 A | 9/1997 | Wyrick | |
| 5,957,897 A | 9/1999 | Jeffrey | |
| 6,409,706 B1 | 6/2002 | Loy | |
| 2003/0057347 A1 | 3/2003 | Weiss | |
| 2004/0039337 A1 | 2/2004 | Letzing | |
| 2004/0078006 A1 | 4/2004 | Bills | |
| 2005/0070848 A1 * | 3/2005 | Kim | A61M 5/2053 604/140 |
| 2006/0141049 A1 | 6/2006 | Lyons et al. | |
| 2007/0202186 A1 | 8/2007 | Yamamoto et al. | |
| 2008/0234637 A1 | 9/2008 | McConnell et al. | |
| 2009/0036827 A1 | 2/2009 | Cazzini | |
| 2009/0148527 A1 | 6/2009 | Robinson et al. | |
| 2010/0104654 A1 | 4/2010 | Robinson et al. | |
| 2010/0249721 A1 * | 9/2010 | Guillermo | A61M 5/2033 604/246 |
| 2011/0238075 A1 | 9/2011 | Clauson et al. | |
| 2012/0271272 A1 * | 10/2012 | Hammack | A61F 9/0017 604/500 |
| 2013/0096534 A1 | 4/2013 | Orilla et al. | |
| 2013/0202186 A1 | 8/2013 | Fang et al. | |
| 2013/0296825 A1 | 11/2013 | Lerner | |
| 2013/0345618 A1 | 12/2013 | Auld et al. | |
| 2015/0351958 A1 | 12/2015 | Contiliano et al. | |
| 2017/0224534 A1 | 8/2017 | Andino et al. | |

FOREIGN PATENT DOCUMENTS

| | | |
|---|---|---|
| EP | 1450884 | 9/2004 |
| EP | 2248494 | 11/2010 |
| GB | 2531910 | 5/2016 |
| GB | 2536517 | 9/2016 |
| JP | H10-507935 | 8/1996 |
| JP | H8-507239 | 8/1998 |
| WO | 2004094823 | 11/2004 |
| WO | 2007100745 | 11/2007 |
| WO | 2009089409 | 7/2009 |
| WO | 2010003011 | 1/2010 |
| WO | WO2010147661 | 12/2010 |
| WO | 2011117592 | 9/2011 |
| WO | 2012051575 | 4/2012 |
| WO | 2012059449 | 5/2012 |
| WO | 2012115911 | 8/2012 |
| WO | 2013028936 | 2/2013 |
| WO | WO2013028936 | 2/2013 |
| WO | 2013151904 | 10/2013 |
| WO | 2013188595 | 12/2013 |
| WO | 2016040635 | 3/2016 |
| WO | 2016042162 | 3/2016 |
| WO | 2016042163 | 3/2016 |

OTHER PUBLICATIONS

Einmabl et al., "Evaluation of a Novel Biomaterial in the Suprachoroidal Space of the Rabbit Eye", IOVS, 2002, 43(5), pp. 1533-1539.
Notice of Allowance dated Mar. 19, 2021 in related U.S. Appl. No. 15/760,717.

* cited by examiner

OPHTHALMIC DELIVERY DEVICE

CROSS-REFERENCE TO RELATED APPLICATIONS

This application is a 35 U.S.C. § 371 national phase application of PCT Application No. PCT/EP15/71520, filed Sep. 18, 2015, which claims priority to U.S. Application No. 62/052,952, filed Sep. 19, 2014, each of which is incorporated herein by reference in its entirety.

RELATED APPLICATIONS

Any and all applications for which a foreign or domestic priority claim is identified in the Application Data Sheet as filed with the present application are hereby incorporated by reference under 37 CFR 1.57. The Ophthalmic Delivery Device of the present invention can be used for delivery of drug compositions such as those described in the Patent Application entitled Ophthalmic Drug Compositions filed simultaneously herewith by Ronald Yamamoto, Stanley Conston and Tien Nguyen. Where allowable, this and all patents and patent applications referred to herein are hereby incorporated by reference.

BACKGROUND OF INVENTION

Due to the unique anatomy and physiology of the eye, multiple barriers exist that prevent significant transport of drugs to ocular tissues. The blood vessels of the eye have restricted permeability due to the blood-ocular barriers that regulate intraocular fluid. Due to these blood-ocular barriers, systemically administered drugs do not reach significant concentration in ocular tissues. Drugs in topical drops administered to the corneal surface are mostly washed out by tears into the naso-lacrimal duct. While in the tear film, drugs have limited time to penetrate the cornea to reach the intraocular space. Some drugs may be delivered to the front, anterior portion of the eye by drops but reaching significant therapeutic concentrations in the posterior portion of the eye and the retina is generally not achieved with topical methods of administration.

Many diseases that result in visual loss involve the posterior retina where color vision and reading occur. To treat the posterior portion of the eye and the posterior retina typically drugs are injected into the eye. Sub-conjunctival injections are used to place a drug depot under the outer surface of the eye, however the very high lymphatic flow in the conjunctiva leads to rapid transport of the drug away from the eye. Sub-conjunctival injections are typically not effective in achieving high drug levels in the posterior portion of the eye.

Sub-Tenon's injections are sometimes used to place the drug in the outer shell of the eye and in a posterior location to deliver drug to the posterior region of the eye. Sub-Tenon's injections have been demonstrated to be useful for the administration of steroids, however the tip of the injection needle is required to be placed deep into the orbit of the eye for posterior delivery, where the tip of the needle cannot be directly observed by the physician. The technique requires experience and careful technique to avoid physical injury to the eye or misplacement of drug.

Intravitreal injections are given to place drug directly into the vitreous chamber, and typically require a smaller quantity of drug as compared to sub-Tenon's injections. The half-life of the drug is limited due to the fluid in the vitreous which continuously moves forward toward the anterior chamber. This vitreous flow washes out the drug over time and contacts the drug to other tissues of the eye in the flow path. Intravitreally administered drugs such as steroids are associated with complications of cataract progression due to drug exposure to the lens and glaucoma from drug exposure to the trabecular meshwork during the anterior flow from the vitreous chamber. In addition, the injection of a typical 50 to 100 microliter fluid drug into the vitreous chamber may cause an acute rise in intraocular pressure from the volume effect, causing discomfort and in some cases requiring treatment.

The suprachoroidal space between the choroid and sclera and the supraciliary space between the ciliary body and sclera are more difficult to locate but also can be used for the injection of drugs. Unlike intravitreal injections, the fluid in the suprachoroidal space and supraciliary space flows posteriorly. This flow may assist drugs injected into the suprachoroidal space or the supraciliary space to reach the posterior tissues and posterior retina.

A variety of injection methods and locations are used to treat the posterior portion of the eye. The selected method may involve the particular properties of the drug to be injected and the target tissues for the drug. Also a preferred injection location and method may be dependent on the pathology of the particular patients, for example, scarring of the retina or the presence of a retinal detachment.

The present invention is directed at devices to facilitate injection of drugs or other materials into the eye. The present invention is especially useful for injection into difficult to locate spaces such as the suprachoroidal space or supraciliary space.

SUMMARY OF THE INVENTION

In keeping with the foregoing discussion, the present invention provides an ophthalmic delivery device for injecting or implanting an injection material into an ocular space or a tissue within a patient's eye. In general, the device is configured with an elongated body having a hollow needle at the distal end. A reservoir holds the injection material to be delivered through the needle. A plunger within the elongated body of the device is acted on by a force element, such as a compression spring, that is configured to provide an injection force to the injection material. The device also comprises a distal element having a distal seal, which also provides a tissue interface. The tissue interface with a closed distal seal is attached to the distal end of the device, sealing the needle lumen during application of the injection force. When the distal end of the device is pressed against a tissue surface of the eye, the distal element is compressed between the eye and the device. In doing so, the elongated body advances towards the distal element and the distal tip of the needle is advanced toward the eye. The needle penetrates the distal seal of the distal element. The penetrated distal element can then slide proximally along the needle to allow advancement of the needle into tissue. The penetrated distal seal opens a flow path permitting the injection of material through the distal end of the needle from the reservoir to the eye. The tissue interface may additionally provide a seal of the needle tract at the injection site. The ophthalmic delivery device therefore automatically acts to discharge the injection material when the distal seal and the ocular tissue are penetrated by the needle. This allows simple one-handed operation of the ophthalmic delivery device. The length, orientation and bevel design of the needle can be chosen to deliver the injection material at a specific depth within the ocular tissue or to a specific space within the ocular tissue such as the subconjunctival space, sub-Tenon space, suprachoroidal space, supraciliary space, vitreous cavity or subretinal space.

The injection material used with the device can be a solid, a semi-solid or a liquid. In a first embodiment of the invention, the ophthalmic delivery device is configured for delivering a solid or semi-solid injection material. The lumen of the needle is configured to serve as the reservoir for the injection material. A push shaft is slidably received within the lumen of the needle to apply an injection force to the injection material. In a second embodiment of the invention, the ophthalmic delivery device is configured for delivering a liquid injection material. The reservoir for the injection material is located within the elongated body of the device and the distal end of the plunger has a plunger seal to apply an injection force to the injection material. Optionally, a Luer fitting or other connector is provided for filling the reservoir with the injection material. A one-way valve prevents backflow of the injection material through the connector.

Some embodiments provide an injection device comprising an elongated body with a hollow needle at the distal end, a reservoir for an injection material to be delivered through the needle, a plunger with a force element or biasing means (such as a spring or compressed gas) that is configured to provide an injection force to said injection material, and a distal element comprising a tissue interface with a distal seal attached to the distal end of the device thereby sealing the needle lumen during application of the injection force, wherein the distal element is secured to the distal end of the needle, wherein the distal seal is penetrable by the distal tip of the needle by the application of pressure on the tissue surface with the distal end of the device, wherein the penetrated distal element becomes slidable on the needle to allow advancement of the needle into tissue, wherein the penetrated distal seal opens a path for flow or delivery of the injection material from the distal end of the needle.

Some embodiments provide an injection device comprising an elongated body with a hollow needle at the distal end, a reservoir for an injection material to be delivered through the needle, a plunger with a force element that provides an injection force to said injection material, and a distal element comprising a tissue interface with a distal seal attached to the distal end of the device thereby sealing the needle lumen during application of the injection force, wherein the distal element is secured to the distal end of the needle. The device may further comprise a second force element or biasing means (such as a spring) disposed between the distal element and the body of the device, wherein the distal seal is penetrable by the distal tip of the needle by the application of pressure on the tissue surface with the distal end of the device, wherein the penetrated distal element becomes slidable on the needle to allow advancement of the needle into tissue, wherein penetration of the distal seal opens a path for flow or delivery of the injection material from the reservoir and through the distal end of the needle into the eye.

Some embodiments provide an injection device comprising an elongated body with a hollow needle at the distal end, a reservoir for an injection material to be delivered through the needle, a plunger with a force element or biasing means that provides an injection force to said injection material, and a distal element comprising a tissue interface with a distal seal attached to the distal end of the device thereby sealing the needle lumen during application of the injection force, wherein the distal element is secured to the distal end of the needle. The device may further comprise a collapsible element disposed between the distal element and the body of the device, wherein the distal seal is penetrable by the distal tip of the needle by the application of pressure on the tissue surface with the distal end of the device, wherein the penetrated distal element becomes slidable on the needle to allow advancement of the needle into tissue, wherein the penetrated distal seal opens a path for flow or delivery of the injection material from the distal end of the needle. These and other aspects of the invention will be made apparent from consideration of the following detailed description in conjunction with the accompanying drawing figures.

DESCRIPTION OF THE INVENTION

Figure 1A:
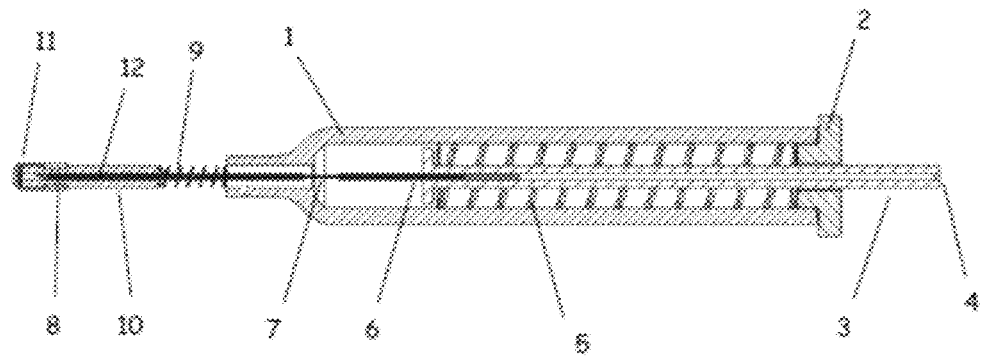
FIG. 1A and FIG. 1B (which contains a pressurized gas 29) depict embodiments of a solid material delivery device.
Figure 1B:
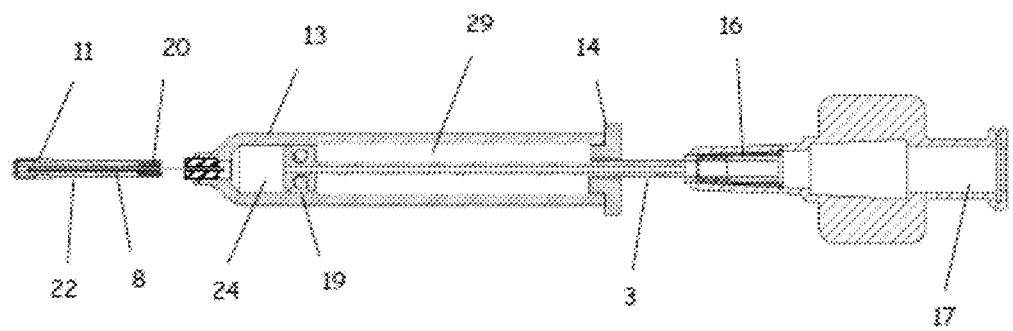

The invention is a device for injection or placement of materials into an eye. The device comprises an elongated body with a hollow needle at the distal end, a slidable plunger at the proximal end, and a reservoir for the material to be injected residing between the needle and the plunger. When a low volume of material is to be injected, the lumen of the needle may also serve as the reservoir or a portion of the reservoir. Alternatively, there may be a reservoir that is separate to the needle lumen, but which is nevertheless in fluid communication with the needle lumen. The reservoir is configured to receive an injection material to be delivered through the needle.

The plunger acts to push the injection material from the reservoir (if separate from the needle lumen), into the needle and through the needle to the desired tissue location. A plunger with a force element is configured to provide an injection force to the injection material. The force element may comprise a spring mechanically coupled to a plunger. The force element may be at least partially within the elongated body of the device. The plunger is mechanically coupled to a source of force such as a spring or pressurized gas reservoir such that an injection force is applied to the injection material within the device after the injection material is placed in the reservoir and prior to insertion into ocular tissues and prior to injection of the injection material into an eye. Secured to the distal end of the needle is a distal element comprising a distal seal, which also acts as a tissue interface. The distal element is moveably secured to the distal tip of the needle where it serves to close off the distal end of the needle to close the path of the injection material from the needle tip. In some embodiments the distal element has a lumen to fit over the outer diameter of the needle. In some embodiments the distal element is secured to the distal tip of the needle through other means. The distal seal of the distal element is distal to the tip of the needle and is configured to be penetrated by the needle as the device is placed on the surface of the eye and is compressed by the user. The needle penetrates the distal seal and inserted into ocular tissue, thereby opening a flow path or path of delivery of the injection material from the reservoir, through the needle and into the eye. The resulting self-actuating injection mechanism insures opening of the delivery path for the injection material immediately when the needle is placed in tissue, regardless of the orientation and speed of needle insertion.

In one embodiment, the distal element comprises a tissue interface and distal seal mounted on a tubular distal housing. The tubular distal housing is fit to the exterior of the needle and may be sealed to the surface of the needle at some point along its length. In one embodiment the housing may be sealed by means of an elastomeric element which is compressed between the housing and the needle. The elastomeric element may therefore be annular. In one embodiment, the elastomeric element may be compressed between the housing and the body of the device. The elastomeric element may reside at or near the proximal end of the housing. In one embodiment the elastomeric element serves as a seal between the housing and the needle. In one embodiment the elastomeric element serves as a frictional element or component which limits the housing travel in the proximal direction to thereby apply a force against the tissue surface by the tissue interface as the needle penetrates the tissues. In some embodiments, the distal element comprises a tissue interface and a distal seal and is slidably attached to the exterior of the needle without a distal housing.

The distal element, which comprises a tissue interface with a distal seal, or a tissue interface with a distal seal and an attached housing, is attached to the distal tip of the needle but is not freely movable or slidable proximally from the end of the needle due to the closed distal seal. After the injection material is loaded into the device, the material comes under pressure from the source of force but cannot move through the distal seal. The tissue interface is placed on the surface of the eye and the device is manually advanced, thereby forcing the needle through the distal seal and then through the external surface of the eye into underlying tissues. The distal element after penetration of the distal seal becomes proximally slidable from the end of the needle to retain the tissue interface on the surface of the eye during advancement of the needle into tissue. When the distal tip of the needle penetrates through the distal seal, the source of force immediately allows for expression of the injection material from the needle tip and into the tissues.

Operation of the device mechanism opens the path for the injection material to move out from the tip of the needle immediately upon penetration through the distal seal which occurs just prior to the entry of the needle into the target tissue. Since the injection material is under pressure prior to penetration of the distal seal by the needle tip, the injection is triggered solely by placement and subsequent advancement of the needle through the tissue interface. This allows precise and automatic control of the timing of the injection action solely due to the needle tip entering the target tissue. The resultant self-actuated mechanism obviates the need for a separate control mechanism, for example a valve or trigger on the body of the injection device, and hence allows for administration of the injection material without the need for special positioning of the fingers or the use of the second hand. The device thereby enables an injection to be performed with a single hand, allowing the other hand of the physician to stabilize the eye or perform other actions to facilitate injection. The self-actuating injection mechanism also eliminates the need for the user to determine when to begin injection which is especially useful when the target tissue space is difficult to locate due to small target size, lack of visualization and anatomic variability.

The device of the present invention allows precise control of the position of the needle by the user during use. The needle is fixed to the body to the device to allow direct control of the distal tip of the needle when the device is held by the body. Since the injection force is provided by the force element, the plunger of the device does not have to be held, triggered or actuated by the hand holding the device, allowing the device to be held and used in a natural, highly controllable position such as with a writing instrument or scalpel. Generally, the needle is arranged parallel to the elongated body or barrel of the device.

Once the device is activated by penetration of the distal seal and insertion into the eye, the injection material cannot flow or move into the eye until a space to accept the injection material is reached by the distal end of the needle. Scleral tissue in particular is very resilient and effectively seals the needle tip during passage of the needle tip to the suprachoroidal or supraciliary space, hence the unique properties of the sclera do not allow for the injection material to enter the sclera. Once an underlying space such as the suprachoroidal space or the supraciliary space is reached by the needle, the injection material is able to flow or move out of the needle to be delivered. By this mechanism the injection material is directed to a location that can accept the injection material at the distal tip of the needle. The delivery of the injection material may be further directed by the tissue interface. The tissue interface may optionally apply a force to the surface of the eye to aid sealing of the needle tract at the surface of the eye. With an appropriate needle length and orientation, the device may be used to inject into the sub-conjunctival space, sub-Tenon's space, suprachoroidal space, supraciliary space, sub-retinal space, the vitreous cavity, or the anterior chamber.

The injection material may be a fluid, solid or semi-solid material. If the injection material is a solid or semi-solid, the material may be loaded into the lumen of the needle with the distal end of the solid or semi-solid in contact with the distal seal provided by the distal element at the distal end of the needle. The needle may extend proximally in the body of the device to provide an extended length of the injection material. A plunger is inserted into the proximal end of the needle and the distal end of the plunger is put into contact with the proximal end of the injection material. Placement of the plunger preloads a force element such as a compression spring acting on the plunger to provide an injection force on the material. In one embodiment, the force element is self-contained in the device or is integrated on the body of the device. In the case of a fluid material for injection, the injection material is placed into the reservoir portion of the body, in a manner similar to a syringe, through a connector, valve or septum in fluid connection to the reservoir. Placement of the injection material in the device preloads a force element such as a compression spring acting on the plunger providing an injection force on the injection material in the reservoir. Other mechanisms may be provided for activating the injection force. For example, the injection force may be activated by a mechanism to compress the force element from the exterior of the device. In another option, the injection force may be activated by mechanically releasing a constrained force element or gas prior to use.

The size of the reservoir, needle and plunger may be sized appropriately for the volume of injection material to be delivered. For a liquid or flowable injection material, the reservoir, needle and plunger may be sized for delivery volumes ranging from 5 microliters to 200 microliters. For the solid or semi-solid injection material, the needle and potentially an extension of the needle into the body of the device may act as the reservoir. The needle and plunger may be sized for solid or semi-solid delivery volumes ranging from 0.1 microliters to 8 microliters.

The needle comprises a stiff material with a diameter to allow the injection material to pass through the lumen of the needle, typically in the range of 20 gauge to 40 gauge (for example less than 0.91 mm outer diameter/0.6 mm inner diameter). The needle is fixed to the body or barrel of the device and does not slide or move in relation to the body to provide precise control of needle depth during penetration of tissues. The distal tip of the needle may be beveled or sharpened to aid penetration. The bevel angle may be designed to facilitate entry into a specific target. For example, a short bevel of 18 degree bevel angle may be used to inject into narrower spaces such as the subconjunctival or sub-Tenon's space. A medium bevel needle of 15 degree bevel angle may be used to inject into spaces such as the suprachoroidal or supraciliary space. Longer bevels, such as 12 degree bevel angle may be used to inject into the anterior or posterior chambers.

In one embodiment, the distal element is designed with a complementary bevel in a lumen of the distal element to provide close apposition of the distal seal to the needle bevel. The bevel of the needle is in alignment with the bevel in a lumen of the distal element. The most distal portion of the distal element may be flat or beveled to aid orientation of the needle during tissue penetration to aid reaching certain injection targets. For example, a beveled tissue contacting surface of the distal element may aid targeting of injections into the tissue targets with less injection depth such as the subconjunctival space, sub-Tenon's space and in some regions of the suprachoroidal space. The angle of the tissue contacting surface of the distal element may range from 90 degrees from the axis of the distal element for perpendicular insertion, to 15 degrees from the axis.

The needle may be constructed from a metal, ceramic, high modulus polymer or glass. The length of the needle in tissue is selected to match the target location for the injection and the variation in target location due to anatomical variability. The effective full length of the needle is the length of the needle distal tip to the distal surface of the tissue interface, when the distal element has achieved full proximal travel. The distal element moves slidably on the needle during injection, allowing for progressive increase in the length of needle protruding through the distal element during advancement into tissue. The injection material is injected automatically once the needle reaches the appropriate location which may be less than the effective full length of the needle. The release of force and resultant time for injection occurs quickly, in approximately 0.1 to 2 seconds depending on the properties of the injection material and the amount of force from the plunger force element. The time for injection may also be controlled by a damping or frictional mechanism coupled to advancement of the plunger to limit the speed of the plunger. The release of force from the force element communicates to the physician with both visible and tactile feedback that there is no need for additional advancement of the needle. The rapid injection event gives the physician sufficient time to halt needle advancement, resulting in an effective variable needle length to accommodate patient to patient differences in tissue thickness. The variable needle length and self-actuation of injection is especially useful for injection into spaces that are not normally open spaces, such as the subconjunctival space, sub-Tenon's space, suprachoroidal space and supraciliary space. For the subconjuctival space and sub-Tenon's space the needle effective full length is in the range of 0.35 mm to 2 mm depending on the angle of needle insertion. For the suprachoroidal space and supraciliary space, the needle effective full length is in the range of 1 mm to 4 mm depending on the angle of insertion. For the vitreous cavity, the needle effective full length is in the range of 10 to 15 mm. The effective full needle length may, for example, be 0.3 mm to 3 mm, 0.35 to 2 mm, 1 mm to 4 mm, 10 to 15 mm.

In one embodiment, the distal element applies a distally directed sealing force against the tissue surface to maintain a seal on the surface of the eye. In one embodiment, the distal element maintains contact with the tissue surface but does not apply a distally directed sealing force against the tissue surface to maintain a seal on the surface of the eye. In one embodiment, the distal element contacts the surface of the eye during penetration of the distal seal of the distal element by the distal tip of the needle but does not maintain contact with the surface of the eye after needle penetration through the distal seal and into ocular tissue. The tissue interface and distal seal may comprise a soft polymer, rubber or other material that allows needle penetration without coring of the material. The tissue interface and distal seal material is selected to provide compliance to both seal to the surface of the eye during insertion of the needle into ocular tissue and also to seal the injection pathway from the needle until the needle is advanced through the distal seal. Once the needle penetrates the distal seal, the needle is advanced through the outer ocular tissues to reach the desired injection site. The tissue interface and distal seal remain on the surface of the eye. The distal seal is sufficiently resilient to prevent rupture by the injection material under pressure prior to advancement of the needle through the distal seal. The portion of the distal seal in the path of the needle is also sufficiently thin to allow penetration by the needle without undue application of force. The distal seal is typically in the range of 250 to 1500 microns in thickness in the region that is penetrated by the needle.

In one embodiment a sealing force is provided by a compression spring between the body of the device and the proximal end of the distal element or distal housing. In one embodiment, the tissue interface provides a sealing force by compression of the tissue interface or elastically compressible elements in the distal element. In one embodiment, the distal element is configured to allow an elastic reduction in length during needle advancement to apply a sealing force. In one embodiment, a friction element disposed in or about the distal element increases the force required to move the distal element proximally thereby promoting contact of the tissue interface with the surface of the eye and maintaining a seal against the eye surface during needle advancement. The friction of the distal element against the needle may be tailored in relation to the proximal movement of the distal element during needle advancement. An increase in friction may be obtained by increased contact or surface texture between the distal element and the external surface of the needle to tailor the amount of force applied by the tissue interface during proximal travel of the interface along the needle length. The friction may be varied along the path of travel of the distal element along the needle. High friction may be provided during the initial path of travel of the distal element to promote contact of the tissue interface to the surface of the eye during initial insertion of the needle into ocular tissues, the friction may be reduced after a length of the needle corresponding to the length of the needle bevel is inserted into ocular tissue. The length of travel of the distal element under the influence of the region of high friction is in the range of 0.3 mm to 2 mm.

In one embodiment, the distal element is attached to the body of the device by one or more collapsible elements. The collapsible element is configured to not allow an increase in length to prevent the distal seal from being displaced from the tip of the needle due to the injection force applied to the injection material prior to penetration of the distal seal. The collapsible element allows a reduction in length, thereby allowing proximal travel of the distal element during advancement of the needle into tissues. In one embodiment, the collapsible element comprises one or more elongated struts that may deform, bend or fold away from the needle during proximal travel of the distal element. In one embodiment, the collapsible element comprises a section of tubing concentric to the needle that has been cut to form openings along the axial length of the tubing to form collapsible struts. The shape and configuration of the collapsible struts may be tailored to provide a desired force-displacement characteristic of the collapsible element. In one embodiment, the collapsible element provides a sealing force which transitions from an increasing spring like force per unit displacement to a constant force independent of displacement to keep the tissue interface and distal seal in sealing contact to the eye surface without undue application of force with further needle advancement into the eye. The transition to a constant force is designed to occur after a length of the needle bevel is inserted into ocular tissue, corresponding to a compression or collapse of the collapsible element of 0.3 mm to 2 mm. In one embodiment, the collapsible element provides for contact of the tissue interface to the surface of the eye during initial insertion of the needle into ocular tissue but collapses to provide little or no resistance to proximal movement of the distal element along the needle after the bevel of the needle is fully inserted into tissue. The collapsible element may be assembled from components in a tubelike configuration or alternatively cut from a segment of tubing such as a laser machined nickel titanium alloy (nitinol) tube. The collapsible element may be disposed between the elongate body and the distal element, such as between the barrel and the housing of the distal element (if present).

Suitable materials for the tissue interface and distal seal include, but are not limited to, natural rubbers, silicone rubbers and thermoplastic elastomers such as polyurethanes. The stiffness of the rubber or elastomer may be selected to provide the appropriate combination of conformance to the tissue surface and sealing of the lumen of the distal end of the needle. The rubber or elastomer must also be capable of penetration by the distal tip of the needle to trigger release of the injection material. Rubbers or elastomers with a Shore A durometer of 25 to 90 are suitable for use as the sealing element. Suitable materials for a distal housing include, but are not limited to, polypropylene, polyethylene, polycarbonate, polysulfone, polyetheretherketone, acrylonitrile butadiene styrene, polystyrene, polyamide, and polyurethanes. Suitable materials for a distal collapsible element include, but are not limited to, stainless steel, spring temper steel, super-elastic nickel titanium alloys, cobalt chrome alloys, oil-tempered chrome silicone, and polyetherimide. In one embodiment, the barrel of the device contains the reservoir and provides an external surface for holding the device during use. The reservoir may comprise a tubular cylinder attached on the distal end to the proximal end of the needle, with a plunger slidably disposed in the lumen of the tubular body. The reservoir may also provide for insertion of a cartridge containing the injection material where the plunger of the device moves a slidable seal in the proximal end of the cartridge to deliver the injection material. The body may be fabricated from a variety of thermoplastic materials suitable for medical use such as polypropylene, polycarbonate, polysulfone, polyethylene, cyclic polyolefins, polystyrene and polymethylmethacryate. The body may incorporate external features such as textures or finger indentations to allow a user to more ergonomically grip and use the device. The body may incorporate index or measurement markings to provide an indication of the amount of material being delivered. The body many incorporate transparent materials or a section of transparent material to allow the visualization of the injection material in the reservoir or movement of the plunger to visually indicate the injection event. The plunger may have markings to aid visualization of reservoir loading and release of injection material.

In embodiments of the invention, the device comprises a means for providing an injection force. Said means as described herein could be, for example, a syringe with a compressible reservoir that can be "squeezed" or compressed by a user (directly or indirectly) to effect injection of material. Alternatively, in a preferred embodiment, the means is a plunger with a biasing means or force element (such as a compression spring or a pressurised gas).

The device may be disposable and/or for single use. Alternatively, the device may be reusable.

The distal seal acts to prevent escape of the injection material from the needle or reservoir when the device is primed (by insertion of injection material into the reservoir) prior to activation by a user. This can be achieved by a hermetic seal between the needle lumen and the outside of the device. This hermetic seal may be achieved by the seal being in direct contact with the needle tip or may be achieved by using a distal element housing that is suitably sized to provide a liquid-tight seal around the needle shaft when placed over the needle tip. For example, the outer diameter of the needle may be complimentary to the inner diameter of the housing to provide a seal.

The person skilled in the art will appreciate the difference between flowable, semi-solid and solid injection materials. Any injection material may be described as flowable if, for example, the kinematic viscosity of the material is less than about 0.002 $m^2/s$ at 20° C. An injection material may be described as semi-solid if, for example, the kinematic viscosity of the material is greater than about 0.002 $m^2/s$ at 20° C.

Generally speaking, and as described above, the device is primed since a pressure or force is placed on the injection material such that once the distal seal is penetrated by the needle and the needle reaches the desired site of delivery in the eye (such as the suprachoroidal space or supraciliary space), the injection material is automatically released. In this way, the device can be operated with one hand. The only force that needs to be applied by the user is the penetration force to allow the needle to penetrate the distal seal and then the eye tissue. The needle length can be suitably designed to target specific injection sites at corresponding depths in the eye. In some embodiments, the device may comprise a retaining means to retain the distal element on the needle once the device is primed.

Prior to injection of the material, the distal element will generally not be in direct physical contact with the elongate body or the barrel. In fact, the distance between the proximal end of the distal element and distal end of the elongate body or barrel (and design of any compressible element that may be present) can be arranged to determine the maximum depth of injection. For example, during operation of the device, as the distal seal is pressed against the eye, the distal element and elongate body or barrel will move towards each other. It is this motion that advances the needle tip towards and through the distal seal/tissue interface and into the patient's eye. Once the proximal end of the distal element abuts against the distal end of the elongate body or barrel (or once the compressible element does not permit further compression), continued advancement of the needle is prevented. Hence, the distance between the proximal end of the distal element and distal end of the elongate body or barrel may be equal to the maximum depth of injection. Account may need to be taken for any distance between the needle tip and the distal seal/tissue interface and/or the use of any compressible element. In particular, the maximum depth of injection may be determined by the distance between the proximal end of the distal element and distal end of the elongate body or barrel less the distance between the needle tip and the distal seal/tissue interface. Thus, the position and sizes of the distal element, needle, and distance between the needle tip and distal seal/tissue interface (if any) can be configured to determine a maximum injection depth. The skilled person could design the device accordingly based on the present disclosure.

In this way the device may comprise a means for determining a maximum injection depth to control the depth of injection of the needle (and hence injection material) into the eye. Said means can be a set distance between the proximal end of the distal element and distal end of the elongate body or barrel (as determined by the relative size of the distal element, the needle, the distance of the needle tip from the distal seal/tissue interface, and the shape and configuration of any compressible element present). Alternatively, the needle may comprise a separate element that halts advancement of the distal element along the needle during operation (such as an element present on the needle disposed between the distal element and the elongate body or barrel, for example an annular ridge or clamp). In some embodiments, this element to prevent further advancement of the distal element along the needle during operation may be moveable such that injection depth can be determined by the user. In such an embodiment, the needle may comprise markings to allow the use to select an appropriate injection depth. In another embodiment, the depth of injection may be determined by the compressible element, for example said compressible element only allowing the desired injection depth by way of increasing rigidity as the element is compressed, or by other mechanical means, such as entrapment of the compressible element between the proximal end of the distal element and distal end of the elongate body or barrel. The present invention therefore provides devices having fixed maximum injection depths suitable for targeting the tissue of interest. Suitable designs to achieve a fixed maximum injection depth would be apparent to the skilled person based on this disclosure. Of course, the depth of injection can be within certain tolerances. Injection depth is also referred to herein as effective needle length.

Figure 2:
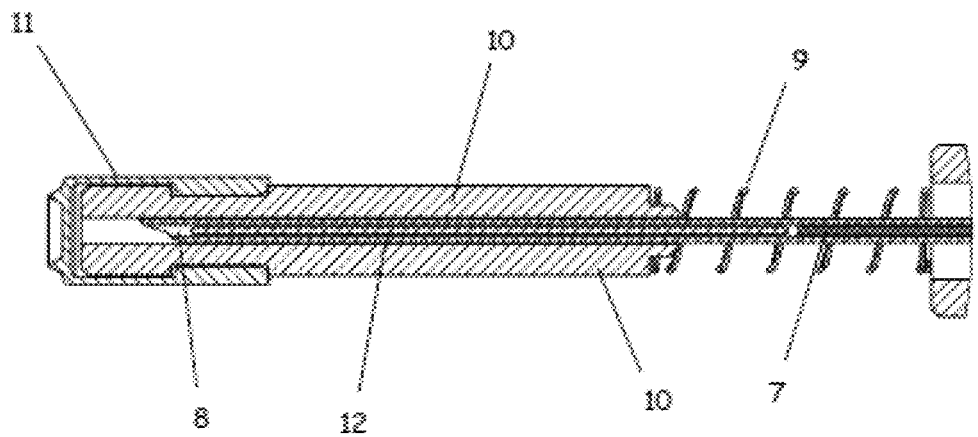
FIG. 2 depicts one embodiment of a distal tip of a solid material delivery device.

In one embodiment, the device is configured to deliver an elongated solid or semi-solid material or implant within the lumen of the needle. Referring to the device depicted in FIG. 1A and the distal tip detail of the device in FIG. 2, the device comprises a hollow barrel 1, with a proximal barrel end cap 2. A plunger 3 slidably passes through the end cap. The plunger has a proximal end 4 which is sealed. A push shaft guide tube 6 is slidably disposed in a lumen in the plunger 3, which provides support for a push shaft 7 to prevent the push shaft from buckling during injection. A plunger compression spring 5, provides a distally directed force on the plunger 3 and push shaft 7. A beveled needle 8, is attached and fixed to the distal end of the barrel 1, such that the needle 8 does not move in relation to the barrel 1 to provide direct control of the location of the needle 8 tip when manipulating the position of the barrel 1. The distal end of the push shaft 7 resides within the lumen of the needle 8 and moves distally when the tissue interface and distal seal 11 is opened by the distal tip of the needle 8. The distal element for the needle 8 comprises a tubular distal housing 10 surrounding the distal end of the needle 8. The tissue interface and distal seal 11 is attached to the distal end of the distal housing 10. A distal housing spring 9, is placed between the distal end of the barrel and the proximal end of the distal housing 10 to provide a distally directed force on the distal housing thereby pressing the tissue interface and distal seal 11 onto the tissue surface.

Figure 3:
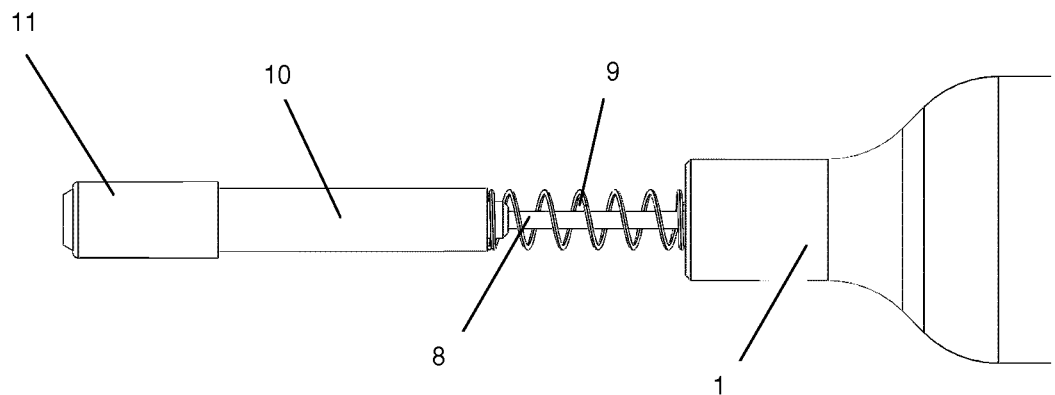
FIG. 3 depicts one embodiment of a distal tip of a delivery device in an uncompressed state.
Figure 4:
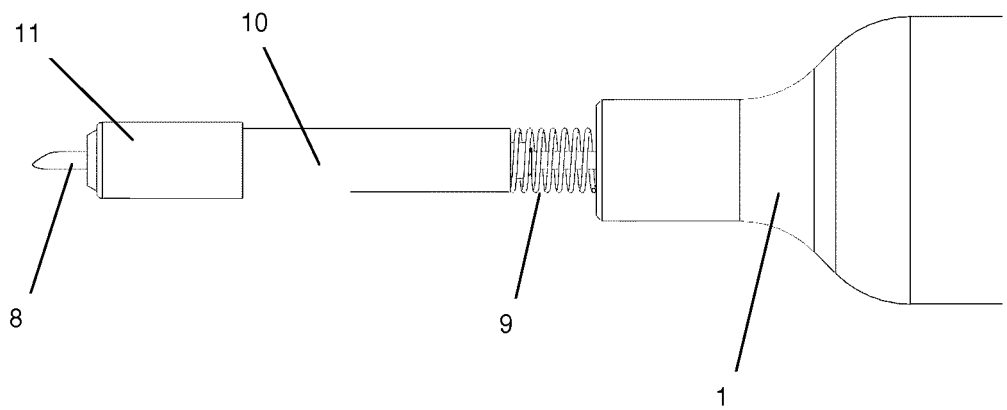
FIG. 4 depicts one embodiment of a distal tip of a delivery device in a compressed state.

As the needle 8 is advanced to penetrate the tissue interface and distal seal 11, the distal housing 10 moves proximally toward the barrel 1 while the needle 8 is advanced into tissue. The distal housing spring 9 acts to maintain pressure of the tissue interface and distal seal 11 as the needle 8 is advanced into tissue. While the tip of the needle 8 is passing through the outer tissues of the eye, the solid or semi-solid injection material 12 or implant within the lumen of the needle 8 is under pressure from compression spring 5 and the path from the distal tip of the needle 8 has been opened, but there is no tissue space for the injection material 12 to be delivered from the needle tip. Once the distal tip of the needle reaches the desired space such as the suprachoroidal space, the supraciliary space or the vitreous cavity the injection material 12 can exit from the needle and is expelled into the space. FIG. 3 shows the distal segment of the device in an uncompressed state. The tissue interface and distal seal 11 and the distal housing 10 are disposed at the end of the uncompressed distal spring 9. The distal spring 9 is anchored to the barrel 1. FIG. 4 shows the distal segment of the device in a compressed state. The force of advancing the device into the tissue causes the distal spring 9 to compress, allowing the distal housing 10 and distal seal 11 and interface to slide proximally along the needle 8. The distal tip of the needle 8 has penetrated the tissue interface and distal seal 11.

Figure 5:
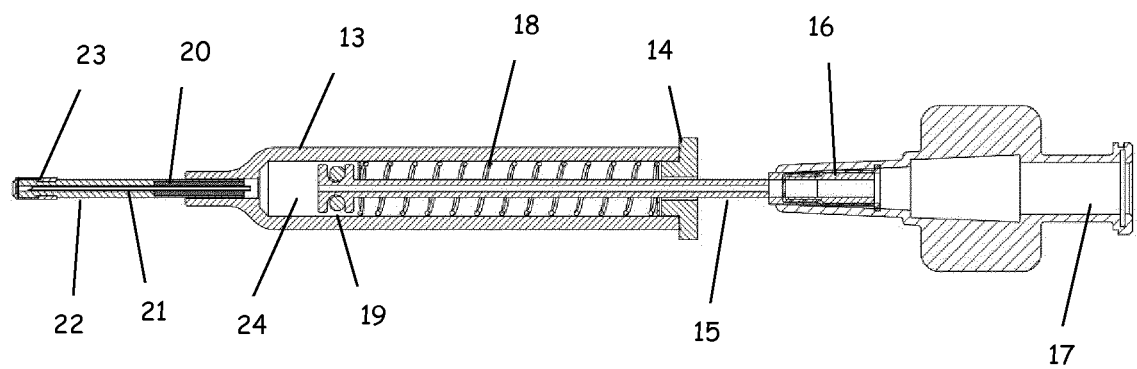
FIG. 5 depicts one embodiment of a fluid delivery device.
Figure 6:
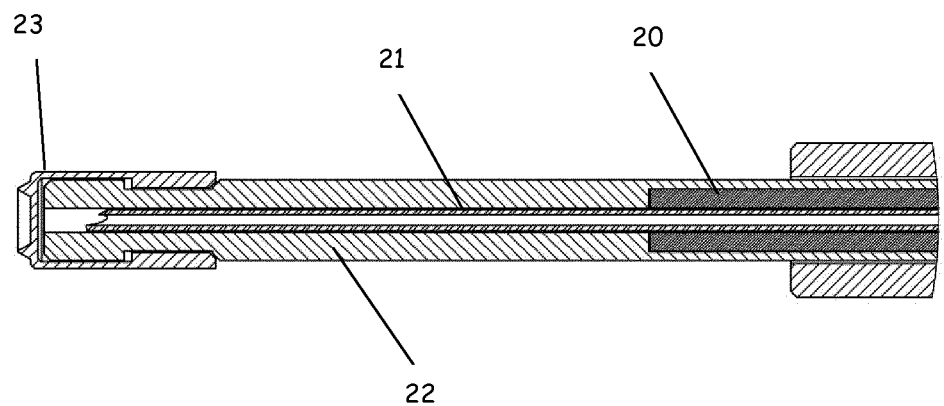
FIG. 6 depicts one embodiment of a distal tip of a fluid delivery device.

In one embodiment, the device is configured to deliver a fluid or flowable material. Referring to the device depicted in FIG. 5 and the distal tip detail of the device in FIG. 6, the device comprises a hollow barrel 13, with a proximal barrel end cap 14. A plunger 15 slidably passes through the end cap and has a plunger seal 19 within the barrel 13. The plunger seal 19 prevents leakage of fluid between the plunger 15 and the barrel 13 inner wall. The distal end of the plunger 15 forms the proximal end of the reservoir 24. The plunger shaft 15 has a fluid path from the distal end, through the plunger seal 19 into the reservoir 24. The proximal end of the fluid path is connected to a female Luer fitting 17. A one-way check valve 16 is placed between the female Luer fitting 17 and the proximal end of the fluid path in plunger shaft 15. A beveled needle 21 is attached and fixed to the distal end of barrel 13 such that the needle 21 does not move in relation to the barrel 13 to provide direct control of the location of the needle 21 tip when manipulating the position of the barrel 13. The plunger 15 moves distally when the tissue interface and distal seal 23 is opened by the distal tip of the needle 21. The distal element of the device comprises a tubular housing 22 surrounding the distal end of the needle 21. The tissue interface and distal seal 23 is attached to the distal end of the distal housing 22. A frictional element in the shape of a tube 20 is disposed in the proximal end of the housing 22 to contact the exterior of the needle 21 and provide means for the tissue interface and distal seal 23 to provide sealing at the injection site. To use the device, the fluid or flowable material to be delivered is injected into the device through the female Luer fitting 17 into reservoir 24. As the fluid or flowable material is placed in the reservoir 24, the plunger travels proximally compressing the compression spring 18. The plunger compression spring 18, provides a distally directed force on the fluid or flowable material, pressurizing the reservoir 24. The check valve 16 provides a proximal seal to the fluid path in the plunger shaft 15 preventing flow out of the female Luer fitting 17. As the needle 21 is advanced to penetrate the tissue interface and distal seal 23, the distal housing 22 moves proximally toward the barrel 13. The tissue interface and distal seal 23 is placed on the surface of an eye and the device is advanced toward the eye. The tissue interface and distal seal 23 is compressed on the surface of the eye and the distal end of the needle 21 is advanced through the distal seal. While the tip of the needle 21 is passing through the outer tissues of the eye, the pressurized injection material in the reservoir 24 has no tissue space to exit the needle tip. Once the distal tip of the needle reaches the target which allows for material flow into a tissue space, such as the suprachoroidal space, supraciliary space or vitreous cavity, the material can exit from the tip of the needle 21 and is expelled from the reservoir 24 into the space or cavity.

Figure 7:
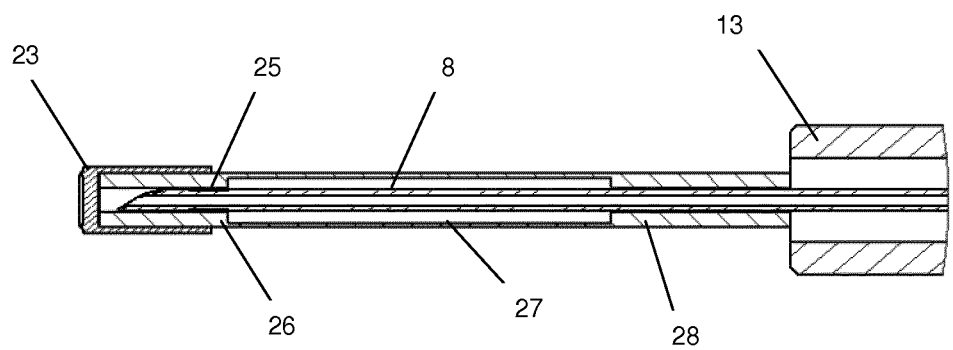
FIG. 7 depicts one embodiment of a distal tip of a delivery device with a collapsible element.
Figure 8:
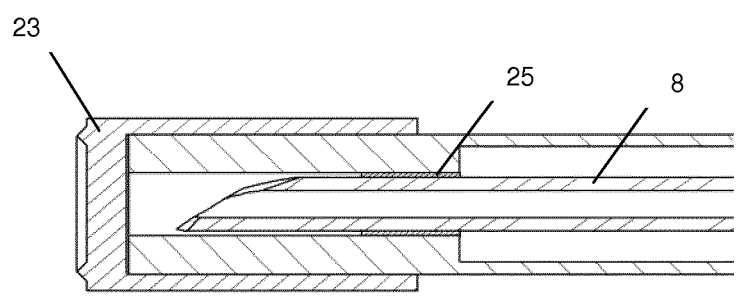
FIG. 8 depicts magnified detail of one embodiment of a distal tip of a delivery device with a collapsible element.
Figure 9:
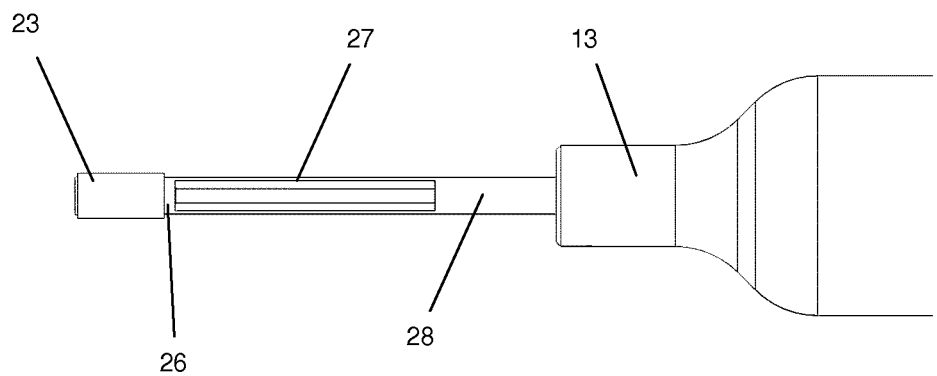
FIG. 9 depicts one embodiment of a distal tip of a delivery device in an uncollapsed state.
Figure 10:
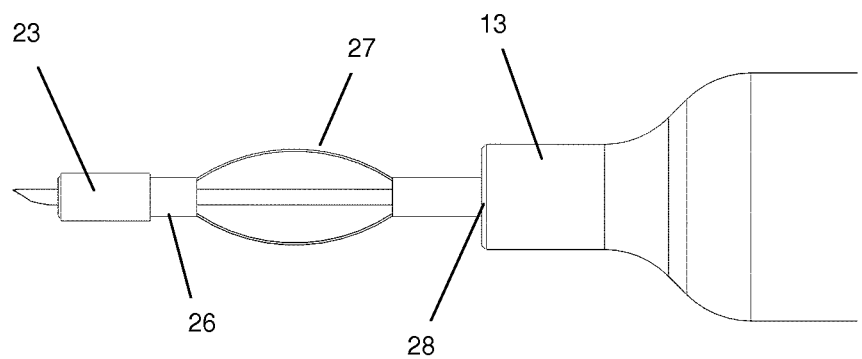
FIG. 10 depicts one embodiment of a delivery device in a collapsed state.

In one embodiment, the distal tip of the device is comprised of collapsible elements. Referring to the device depicted in FIG. 7 and the magnified device distal tip detail in FIG. 8, the distal tip is comprised of distal segment, a central collapsible segment and a proximal segment. The tissue interface and distal seal 23 is disposed about a distal tubular shaft 26. The inner lumen of the distal tubular shaft 26 contains an internal seal 25 which seals the space between the tubular distal shaft 26 and the bevelled needle 8. The central segment is comprised one or more segments 27 which function as collapsible elements which can impart a force against the tissue surface during use. The collapsible elements 27 are attached or integral to the distal tubular shaft 26 and proximal tubular shaft 28. The proximal tubular shaft 28 is connected to the barrel 13 of the device providing an anchor point for the collapsible element and preventing distal movement of the tissue interface and distal seal 23. FIG. 9 shows the distal segment of the device in an uncollapsed state. The tissue interface and distal seal 23 and the distal tubular shaft 26 are disposed at the end of the collapsible elements 27. The proximal tubular shaft 28 is anchored to the barrel 13. FIG. 10 shows the distal segment of the device in a collapsed state. The force of advancing the device into the tissue causes the collapsible elements 27 to deform, allowing the distal tubular shaft 26 and tissue interface and distal seal 23 to slide proximally along the needle 8. The distal tip of the needle 8 has penetrated the tissue interface and distal seal 23.

The described embodiments of the device may be used in combination to deliver a solid, semi-solid or liquid. The configuration of the distal portion of the device comprises the distal element comprising the tissue interface and distal seal on the distal end of the needle. The use of a distal compression spring, frictional element, a collapsible element, or a combination of such elements in conjunction with the distal element may be used for delivery of a solid, semi-solid or liquid.

For use in the device for delivery of a solid or semi-solid, a lubricant may be used to aid injection. The lubricant may be used to coat the solid or semi-solid injection material or the needle lumen. The lubricant may also be placed in the lumen of the distal element to coat the tip of the injection material and the outer surface of the needle as it passes into tissue. Suitable lubricants include, but are not limited to, oils, waxes, lipids, fatty acids and low molecular weight polymers. Low molecular weight polymers include, but are not limited to, polyethylene glycol and polysiloxane.

A variety of drugs may be delivered by the present invention to the eye for the treatment of ocular diseases and conditions including inflammation, infection, macular degeneration, retinal degeneration, neovascularization, proliferative vitreoretinopathy, glaucoma and edema. Useful drugs include, but are not limited to, steroids, non-steroidal anti-inflammatory agents, antibiotics, VEGF inhibitors, PDGF inhibitors, anti-TNF alpha agents, mTOR inhibitors, cell therapies, neuroprotective agents, anti-hypertensive agents, antihistamines, aminosterols and nucleic acid based therapeutics. The drugs may be in the form of soluble solutions, suspensions, gels, semi-solids, microspheres or implants. In one embodiment, the drug is preloaded in the device prior to use during the time of manufacture. The source of force to provide an injection force to the injection material may be activated just prior to use. In one embodiment the activation is achieved by a mechanism to preload the force element, such as compressing a spring, from the exterior of the device such as by a movable proximal handle attached to the plunger. In one embodiment, the source of force is preloaded during manufacture when the drug is placed in the device and the preloaded force is stabilized by means of a stop mechanism. Prior to use, the stop mechanism is released, thereby placing the force on the injection material prior to contact or penetration of the eye and the injection is triggered by the advancement of the needle through the tissue interface and distal seal as with the previous embodiments of the invention.

In one embodiment of the invention there is provided an injection device for fluid, solid or semi-solid injection material comprising an elongate body having a hollow needle at its distal end. The distal end of the needle is housed in a distal element having a distal seal that seals the lumen on the needle preventing any injection material from being released. The device also comprises a reservoir, either formed from the lumen of the needle or being disposed in the elongate body of the device but in fluid communication with the lumen of the needle. The device is primed by introduction of injection material into the reservoir. The device has a collapsible element housed between the distal element and the elongate body, which serves to retain the distal element on the needle, whilst allowing compression of the distal element along the length of the needle and toward the elongate body when the device is activated. In use, the distal element is placed on the surface of the eye and a pressure applied by the user. This causes the needle tip to advance towards and penetrate the distal seal, thereby allowing injection material to be dispensed from the distal end of the needle. However, the material will only be dispensed once the needle tip reaches a void in the target tissue of the eye. The pressure applied on the injection material when the device is primed allows injection of the material to the target site automatically and with the use of only one hand. The needle length and/or length of the collapsible element (and hence distance between the proximal end of the distal element and elongate body) can be configured appropriately to target different spaces at different depths within the eye.

The invention will now be described by way of specific examples, which are intended to be illustrative and not limiting on the scope of the invention.

EXAMPLES

Example 1: Solid Material Delivery Device

A device according to one embodiment of the invention was fabricated to inject a solid material into the suprachoroidal space or supraciliary space of the eye. A body and attached needle was fabricated by cutting off the proximal end of a 0.5 ml insulin syringe with a mm long 27 gauge integral hypodermic needle to a barrel length of 30 mm. The proximal open end of the syringe barrel was tapped for an 8-32 thread. A barrel end cap was fabricated from plastic with a through hole sized to fit the plunger shaft and an external thread of 8-32. A plunger was fabricated from a metal tube with an outer diameter of 1.52 mm and an inner diameter of 0.25 mm. The distal end of the plunger was comprised of two flanges welded to the end with a gap of 1 mm between them. A silicone 0-ring seal was placed between the flanges. A compression spring with a 0.20 N/mm spring force, an outer diameter of 2.6 mm and a wire diameter of 0.25 mm was placed over the shaft of the plunger and the barrel end cap was then slid over the plunger shaft proximal to the spring. A solid push shaft of 0.18 mm diameter was fixed in the lumen of the plunger shaft extending distally such that the tip of the push shaft just protruded from the distal tip of the needle when the device was fully assembled and the plunger was in the most distal travel position.

A housing 9.5 mm long with a 1.5 mm outer diameter and a 0.35 mm inner diameter was fabricated from polycarbonate tubing, with a sealing element disposed in the proximal end of the housing. The housing length was such that the distal tip of the housing extended 2 mm beyond the tip of the needle when assembled. A molded tissue interface and distal seal 3.5 mm long with an outer diameter of 1.9 mm and an inner diameter of 0.9 mm was fabricated from 50 Shore A durometer silicone rubber. The tissue interface and distal seal was placed over the distal end of the housing. A housing compression spring of 0.08 N/mm spring force, with an outer diameter of 1.5 mm and a wire diameter of 0.1 mm was placed over the needle to provide sealing force against the tissues. The housing compression spring had a free length of 4.8 mm and a compressed length of 0.8 mm. The spring was placed over the needle, and then the housing and seal were placed over the needle.

Example 2: Use of Solid Material Delivery Device

A device according to Example 1 was used to deliver a solid polymer material through a model of the external tissue of the eye to allow visualization of the injection. A hollow spherical article fabricated from silicone elastomer with a durometer of 50 Shore A and a thickness of 1 mm was used to simulate the conjunctiva and sclera of an eye.

The housing, tissue interface and distal seal was temporarily removed from the needle. The plunger and push shaft was retracted proximally and a length of 5-0 polypropylene suture, 9.6 mm in length to act as a solid injection material was inserted into the distal tip of the needle. The polypropylene suture was used as a model for a solid drug containing material. The housing, tissue interface and distal seal were placed back on the needle tip after placement of the suture.

The tissue interface and distal seal of the device was placed against the surface of the model eye and the needle was manually advanced by pushing on the barrel. When the needle had pierced the distal seal and through the model surface tissue, the length of suture was immediately expelled from the needle into the space beneath the model surface tissue without further manipulation of the injection device.

Example 3: Solid Material Delivery Device

A device according to an embodiment of the invention was fabricated to inject a solid or semi-solid material into the suprachoroidal or supraciliary space of the eye. A barrel element was fabricated by cutting off the proximal end of a 0.5 ml insulin syringe to a barrel length of 30 mm. The integral needle was removed from the barrel to allow the attachment of standard Luer hub needles. The distal tip of the barrel was cut off leaving a remaining section of Luer taper capable of securely holding a Luer hub needle. A barrel end cap was fabricated from a nylon 10-32 socket head cap screw with a thread length of 4.5 mm. A through hole of 1.86 mm diameter was drilled through the end cap to allow the plunger to freely slide through the end cap. A plunger was fabricated from a tubular stainless steel rod with an outer diameter of 1.8 mm and an inner diameter of 0.8 mm and a length of 43 mm. The distal end of the rod was turned down to a diameter of 1.74 mm and a stainless steel washer of 4.1 mm outer diameter, 1.70 mm inner diameter and 0.5 mm thickness was press-fit onto the rod to provide a distal stop for the plunger spring. The proximal end of the rod was drilled out to 1.55 mm diameter.

A straightened stainless steel wire 0.25 mm diameter and 80 mm long was used as a push shaft to expel the delivery material from the device. A section of polyetheretherketone (PEEK) capillary tubing with an outer diameter of 1.57 mm, an inner diameter of 0.25 mm and a length of 2.25 mm was used as a securing element for the wire push shaft. The lumen of the PEEK securing element was sufficiently tight enough on the wire push shaft to hold it securely in place under normal use, but allowed the push shaft to be slidably adjusted using moderate force with needle nosed pliers. The push shaft wire was inserted through the PEEK securing element and then the securing element was press-fit into the drilled out proximal end of the plunger rod with the wire push shaft extending through the lumen of the plunger rod. A compression spring with an outer diameter of 3.1 mm and a wire diameter of 0.18 mm and a length of 31.8 mm was placed over the shaft of the plunger and the barrel end cap was then slid over the plunger shaft proximal to the spring. The plunger and push shaft assembly was placed into the barrel housing with the push shaft extending through the distal tip of the barrel. The end cap was press fit into the barrel proximal end securing the plunger assembly within the barrel. A 27 gauge by 13 mm hypodermic needle (Nipro Corporation, Model AH+2713) was placed over the distal end of the wire push shaft and pressed onto the barrel distal Luer taper. The lumen of the 27 gauge needle allowed for a close sliding fit with the wire push shaft. Once assembled, the length of the push shaft was manually adjusted so that the tip of the push shaft was at the same level as the distal tip of the 27 gauge needle.

A safety mechanism was incorporated into the device to prevent premature activation of the plunger by the plunger spring force. Two shallow grooves 180 degrees apart and perpendicular to the axis of the plunger were made in the plunger at a distance of 19 mm from the distal tip. The distance between the groove faces was 1.5 mm. A securement clip was fabricated from brass sheet with a width of 6.3 mm and a length of 18 mm. A slot with a width of 1.6 mm and a length of 8.8 mm was machined into the securement clip. The slot was cut in the center of the short side of the securement clip and traversing in the long axis direction.

For use, the plunger was retracted thereby compressing the plunger spring until the plunger grooves were exposed proximally to the end cap. The securement clip was placed over the plunger such that the slot on the securement clip engaged the grooves on the plunger shaft. The securement clip then was held against the proximal end surface of the end cap by the spring force, preventing movement of the plunger.

Example 4: Solid Material Delivery Device

A device according to Example 3 was fabricated. A molded cylindrical tissue interface and distal seal element was fabricated from 70 Shore A durometer silicone rubber. The distal element had a length of 3.7 mm and a diameter of 1.75 mm. The distal element had a lumen of 2.7 mm length and 0.38 mm diameter. The distal end of the lumen of the distal element was configured with a beveled shape which conformed to the bevel on the distal end of a 27 gauge needle. The distal element was attached to the distal tip of the needle such that the needle bevel was in contact with the lumen bevel in order to seal the distal tip of the needle. The non-beveled section of the lumen acted as a slidable seal on the shaft of the needle and provided enough frictional force against the needle shaft to maintain the distal tip against the eye surface during advancement of the needle through the distal seal of 1 mm thickness.

Example 5

A device according to an embodiment of the invention was fabricated to inject a solid or semi-solid material into the subconjunctival space of the eye. A barrel element was fabricated by cutting off the proximal end of a 0.5 ml insulin syringe to a barrel length of 30 mm. The integral needle was removed from the barrel to allow the attachment of a modified needle for subconjunctival injection. The distal tip of the barrel was cut off leaving a remaining section of Luer taper capable of securely holding Luer hub of the needle. A barrel end cap was fabricated from a nylon 10-32 socket head cap screw with a thread length of 4.5 mm. A through hole of 1.86 mm diameter was drilled through the end cap to allow the plunger to freely slide through the end cap. A plunger was fabricated from a tubular stainless steel rod with an outer diameter of 1.8 mm and an inner diameter of 0.8 mm and a length of 43 mm. The distal end of the rod was turned down to a diameter of 1.74 mm and a stainless steel washer of 4.1 mm outer diameter, 1.70 mm inner diameter and 0.5 mm thickness was press-fit onto the rod to provide a distal stop for the plunger spring. The proximal end of the rod was drilled out to 1.55 mm diameter.

A stainless steel wire 0.20 mm diameter and 80 mm long was used as a push shaft to expel the delivery material from the device. A section of polyetheretherketone (PEEK) capillary tubing with an outer diameter of 1.57 mm, an inner diameter of 0.25 mm and a length of 2.25 mm was used as a securing element for the wire push shaft. The push shaft wire was inserted through the PEEK securing element and then the securing element was press-fit into the drilled out proximal end of the plunger rod with the wire push shaft extending through the lumen of the plunger rod. A compression spring with an outer diameter of 3.1 mm and a wire diameter of 0.2 mm and a length of 31.8 mm was placed over the shaft of the plunger and the barrel end cap was then slid over the plunger shaft proximal to the spring. The plunger and push shaft assembly was placed into the barrel housing with the push shaft extending through the distal tip of the barrel. The end cap was press fit into the barrel proximal end securing the plunger assembly within the barrel. A custom 27 gauge by 13 mm hypodermic needle fabricated with an 18 degree bevel angle, short bevel needle was placed over the distal end of the wire push shaft and pressed onto the barrel distal Luer taper. The lumen of the 27 gauge needle allowed for a close sliding fit with the wire push shaft. Once assembled, the length of the push shaft was manually adjusted so that the tip of the push shaft was at the same level as the distal tip of the 27 gauge needle and then the push shaft was adhesively bonded into place at the securing element.

A safety mechanism was incorporated into the device to prevent premature activation of the plunger by the plunger spring force. Two shallow grooves 180 degrees apart and perpendicular to the axis of the plunger were made in the plunger at a distance of 19 mm from the distal tip. The distance between the groove faces was 1.5 mm. A securement clip was fabricated from brass sheet with a width of 6.3 mm and a length of 18 mm. A slot with a width of 1.6 mm and a length of 8.8 mm was machined into the securement clip. The slot was cut in the center of the short side of the securement clip and traversing in the long axis direction.

For use, the plunger was retracted thereby compressing the plunger spring until the plunger grooves were exposed proximally to the end cap. The securement clip was placed over the plunger such that the slot on the securement clip engaged the grooves on the plunger shaft. The securement clip then was held against the proximal end surface of the end cap by the spring force, preventing movement of the plunger.

A molded cylindrical tissue interface and distal seal element was fabricated from 70 Shore A durometer silicone rubber. The distal element had a length of 3.7 mm and a diameter of 1.75 mm. The distal element had a lumen of 2.7 mm length and 0.41 mm diameter. The distal end of the lumen of the distal element was configured with a beveled shape which conformed to the bevel on the distal end of the 27 gauge needle. The distal tip of the element was beveled at a 20 degree angle parallel to the angle in the distal tip of the lumen. The distal element was attached to the distal tip of the needle such that the needle bevel was in contact with the lumen bevel in order to seal the distal tip of the needle. The non-beveled section of the lumen acted as a slidable seal on the shaft of the needle and provided enough frictional force against the needle shaft to maintain the distal tip against the eye surface during advancement of the needle through the distal seal.

Example 6: Use of Solid Material Delivery Device

A device according to Example 4 was fabricated. A solid element for delivery was fabricated by extruding a slurry comprised of drug loaded microspheres in a carrier material. The drug loaded microspheres comprised polylactic-glycolic acid copolymer spherical particles in the range of 10 to 20 microns in diameter. The microspheres were loaded with 25 weight % fluocinolone acetonide, a corticosteroid. A slurry for extrusion was formulated using 85 weight % microspheres and 15 weight % binder. The binder was formulated from 92 weight % high molecular weight, K90 polyvinylpyrrolidone and 8 weight % low molecular weight, K12 polyvinylpyrrolidone, which was in a solution of 25 weight % concentration in de-ionized water. The slurry was dispensed using a 0.3 ml syringe with a distal needle of 0.25 mm inner diameter at a pump speed of 50 microliters/min using a syringe pump to extrude filaments of similar diameter to the inner diameter of the dispensing needle. The filaments were allowed to dry at ambient conditions prior to further processing. To aid in the localized delivery of the solid element in the target space, the microsphere containing filament was cut into segments and loaded into the delivery device. The segments were cut in various decreasing lengths so as allow the length of filament segments to buckle or move laterally in the suprachoroidal space. The segment lengths from distal to proximal were as follows: 1 mm, 2 mm, 2 mm, 3 mm, and 4 mm for a total length of 12 mm.

A cadaver porcine eye was prepared by inflating the posterior chamber to a pressure of approximately 20 mm Hg. A target injection location 5.5 mm posterior of the limbus of the eye was chosen for injection. The securement clip was removed from the plunger shaft. The tissue interface and distal seal was placed against the scleral surface and the needle tip was then advanced through the distal seal and into the tissues. Once the needle lumen reached the suprachoroidal space, the segmented solid element was free to exit the needle and was expelled by the push shaft under the plunger spring force. The delivery of the solid element was confirmed by manually excising a flap in the sclera to expose the suprachoroidal space. A sample of the fluid in the suprachoroidal space was taken and placed on a microscope slide. Examination of the slide under the microscope at 100× magnification revealed numerous microspheres that had been released from the filament injected into the suprachoroidal space.

Example 7: Use of Solid Material Delivery Device

A device according to Example 4 was fabricated. A solid element for delivery was fabricated by dissolving polylactic acid polymer in chloroform at a concentration of 16.7 weight %. After the polymer was dispersed in solution, a corticosteroid, dexamethasone, was added to the dispersion in a concentration of 60 weight % of the solids content. The dispersion was then used to extrude a filament for use in the device. The dispersion was dispensed using a 0.3 ml syringe with a distal needle of 0.25 mm inner diameter at a pump speed of 50 microliters/min using a syringe pump. The filament had a diameter similar to the inner diameter of the dispensing needle. The filament was allowed to dry and then cut into segments 12 mm in length, corresponding to approximately 0.59 microliters of volume.

The device was prepared for use by retracting the plunger against the spring force and holding it in place with the securement clip. A filament solid element was placed in to the lumen of the 27 gauge needle. A tissue interface and distal sealing element was fabricated similar to Example 5 with the exception that the distal end was cut at a 60 degree angle parallel to the lumen bevel angle to allow for an angled approach to the surface of an eye. The distal element was placed over the distal tip of the needle to seal the needle lumen and prevent premature release of the solid element.

A cadaver porcine eye was prepared by inflating the posterior chamber to a pressure of approximately 20 mm Hg. A target injection location 6 mm posterior of the limbus of the eye was chosen for injection. The securement clip was removed from the plunger shaft. The end of the distal element was placed against the eye and the device was advanced. The needle penetrated the distal seal and entered the tissues of the eye. Once the needle lumen reached the suprachoroidal space, the solid element was free to exit the needle and was expelled by the push shaft under the plunger spring force. The delivery of the solid element was confirmed by excising a flap in the sclera to expose the suprachoroidal space, which revealed the solid filament in the suprachoroidal space.

A live porcine subject was prepared for use of the device loaded with the solid filament. The subject was placed under general anesthesia and the eye stabilized with a traction suture. The location of the suprachoroidal space was verified by injection of a small amount of air with a thirty gauge needle in the region of the pars plana. The device was positioned with the distal tip on the surface of the eye and the securement clip removed. The needle was advanced through the distal sealing element and into the eye. Once the tip of the needle had reached the suprachoroidal space, the drug containing filament was injected into the space.

Example 8: Use of Solid Material Delivery Device

A Device according to Example 4 was fabricated. A solid element for delivery was fabricated by extruding a slurry comprised of drug loaded microspheres in a carrier material. The drug loaded microspheres comprised polylactic-glycolic acid copolymer spherical particles in the range of 10 to 20 microns in diameter. The microspheres were loaded with 28 weight % Everolimus, a protein kinase inhibitor. A slurry for extrusion was formulated using 85 weight % microspheres and 15 weight % binder material. The binder material was comprised of 89 weight % high molecular weight K90 polyvinylpyrrolidone, 7 weight % low molecular weight K12 polyvinylpyrrolidone and 4 weight % d-alpha tocopheryl polyethylene glucol succinate (Vitamin E-TPGS) which was in a solution of approximately 25 weight % concentration in de-ionized water. The slurry was dispensed using a 0.3 ml syringe with a distal needle of 0.25 mm inner diameter at a pump speed of 15 microliters/min using a syringe pump to extrude filaments of similar diameter to the inner diameter of the dispensing needle. Filaments were allowed to dry at ambient conditions prior to cutting into segments 12 mm long, corresponding to approximately 0.59 microliters of volume.

The device was prepared for use by retracting the plunger against the spring force and holding in place with the securement clip. A filament solid element was placed in to the lumen of the 27 gauge needle. A tissue interface and distal sealing element was fabricated similar to Example 5 with the exception that the distal end was cut at a 60 degree angle parallel to the lumen bevel angle to allow for an angled approach to the surface of an eye. A tissue interface and distal seal was placed over the distal tip of the device needle preventing premature release of the solid element.

A human cadaver eye was prepared by inflating the posterior chamber to a pressure of approximately 15 mm Hg. A location 2.5 mm posterior of the limbus in the superior-temporal quadrant was marked with a surgical caliper, the location being in the region of the pars plicata, superficial to the ciliary body. The tissue interface of the device was placed against the scleral surface and the safety clip removed. The needle tip was advanced through the distal seal and into the tissues until the needle tip reached the supraciliary space, at which point the plunger advanced the solid element into the space under the force of the plunger spring without manipulation by the operator to trigger injection.

A perfusion bottle of phosphate buffered saline (PBS) was set at a height to deliver 15 mm Hg of fluid pressure to a 30 gauge hypodermic needle. The needle was inserted through the cornea of the cadaver eye, into the anterior chamber and the PBS was allowed to perfuse the eye for 20 hours. After the perfusion, the eye was examined to evaluate the flow of microspheres posteriorly from the injection site. The sclera was carefully dissected away from the ciliary body and choroid and completely removed. The location of the injection could readily be seen as a large somewhat diffuse concentration of microspheres present on the surface of the choroid and extending in a line posteriorly. Using a glass capillary tube, fluid samples were taken of the choroidal surface in the posterior region below the implantation site, approximately 8-10 mm anterior of the optic nerve. The swabs were transferred to a glass microscope slide and examined for the presence of microspheres at 100× magnification. Microspheres were seen in the liquid samples from the posterior region of the eye.

Example 9: Fluid Delivery Device

A device according to one embodiment of the invention was fabricated to inject a fluid into the suprachoroidal space or supraciliary space of the eye. A body and attached needle was fabricated by cutting off the proximal end of a 1.0 ml insulin syringe with 12.7 mm long 27 gauge integral needle to a barrel length of 32 mm. The proximal open end of the syringe barrel was tapped for a 10-32 thread. A barrel end cap was fabricated from plastic with a through hole sized to fit the plunger shaft and an external thread of 10-32. A plunger was fabricated from a metal tube with an outer diameter of 2.4 mm and an inner diameter of 0.4 mm. The distal end of the plunger comprised two flanges welded to the end and with a gap of 1.3 mm between them. A silicone O-ring seal was placed between the flanges. A compression spring with a spring force of 0.33 N/mm, an outer diameter of 4.6 mm and a wire diameter of 0.4 mm was placed over the shaft of the plunger and the barrel end cap was then slid over the plunger shaft proximal to the spring. The proximal end of the plunger comprised a larger diameter tube sized to allow the insertion of a rubber duck-bill style check valve which was welded to the plunger shaft after assembly of the plunger spring and end cap. The valve was inserted into the larger tube and a female Luer lock fitting was attached over the tube and valve.

A housing 9.5 mm long with a 1.5 mm outer diameter and a 0.35 mm inner diameter, was fabricated from polycarbonate tubing, with a sealing element disposed in the proximal end of the housing. The housing length was such that the distal tip of the housing extended 2 mm beyond the tip of the needle when assembled. A molded tissue interface and distal seal element 3.5 mm long with an outer diameter of 1.9 mm and an inner diameter of 0.9 mm was fabricated from 50 Shore A durometer silicone. The tissue interface and distal seal was placed over the distal end of the housing. A housing compression spring of 0.08 N/mm spring force, an outer diameter of 1.5 mm and a wire diameter of 0.1 mm was placed over the needle to provide sealing force against the tissues. The housing compression spring had a free length of 4.8 mm and a compressed length of 0.8 mm. The spring was placed over the needle, then the housing and tissue interface and distal seal were placed over the needle and the spring was adhesively bonded to the proximal end of the housing at one end and the syringe barrel at the other end.

Example 10: Fluid Delivery Device

A device with a barrel and plunger according to Example 9 was fabricated. A distal housing with a collapsible element was fabricated from stainless steel and nickel-titanium (nitinol) superelastic metal alloy. The housing and collapsible element consisted of proximal and distal stainless steel tubular shafts with two flat, extended segments of nitinol connecting the tubular shafts together. The flat elements formed collapsible elements between the distal and proximal tubular shafts. The proximal shaft was 3.5 mm long and the distal shaft was 2.5 mm long. The tubular shafts were fabricated from two segments of stainless steel tubing, an inner segment of 0.48 mm inner diameter and 0.68 mm outer diameter, and an outer segment of 0.78 mm inner diameter and 1.06 mm outer diameter. The two flat segments of nitinol were placed 180 degrees apart and assembled by press fitting the two tubular shaft segments together, trapping the flat nitinol segments between them. The flat segments were 0.6 mm wide and 0.2 mm thick and after assembly 7.5 mm long. The proximal end of the inner lumen of the distal tubular shaft was sealed by injecting a small amount of 50 Shore A durometer silicone rubber into the lumen and then curing it at 150 degrees C. for 10 minutes. A tissue interface and distal seal was fabricated according to Example 7 and was placed over the outside of the distal tubular shaft. The housing assembly was placed over the needle of the device and the needle tip was pushed through the cast inner lumen seal, thereby placing the collapsible element between the tissue interface with distal seal and the body of the device. The two sealing elements effectively sealed the distal tip of the needle within the distal tubular shaft. The collapsible element prevented travel of the distal element distally, but allowed for travel proximally during needle advancement by collapse of the flat segments of nitinol.

Figure 11:
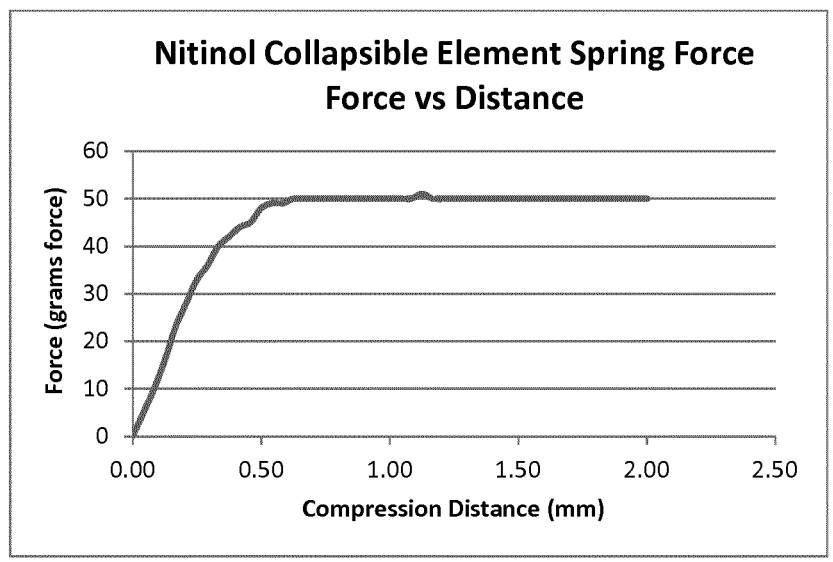
FIG. 11 depicts a plot of the force versus displacement of a distal element with a collapsible element.

A mechanical testing machine was used to determine the force profile for the distal housing with the collapsible element. An assembled distal housing with the collapsible element was placed over a 27 gauge by 25 mm long needle. The needle was mounted in the lower clamp of the mechanical tester. The upper clamp was configured to allow the needle to slide freely in the clamp and have the jaws of the clamp engage the distal tip of the tissue seal. The mechanical test machine cross-head was set to a compression speed of 25 mm/min. The collapsible distal housing was compressed for a distance of 2.0 mm. Five sample runs were performed and the results were averaged. FIG. 11 presents the averaged results of the force testing of the housing. In the first 0.5 mm of travel the force increased linearly at an average spring rate of 1.07 N/mm. After 0.5 mm of travel the force remained constant at average of 0.49 N.

Example 11: Fluid Delivery Device

A device according to one embodiment of the invention was fabricated to inject a fluid into the suprachoroidal space or supraciliary space of the eye. A body and attached needle was fabricated by cutting off the proximal end of a 1.0 ml insulin syringe with 9.5 mm long 30 gauge integral needle to a barrel length of 34 mm. The proximal open end of the syringe barrel was tapped for an 8-32 thread. A barrel end cap was fabricated from a plastic cap screw with a through hole sized to fit the plunger shaft and an external thread of 8-32. A plunger was fabricated from a metal tube with an outer diameter of 2.4 mm and an inner diameter of 0.4 mm. The distal end of the plunger comprised two flanges welded to the end and with a gap of 1.3 mm between them. A silicone O-ring seal was placed between the flanges. A compression spring with a spring force of 0.33 N/mm, an outer diameter of 4.6 mm and a wire diameter of 0.4 mm was placed over the shaft of the plunger and the barrel end cap was then slid over the plunger shaft proximal to the spring. The proximal end of the plunger was press-fit into a duck-bill check valve (Qosina, Inc, Part number 80088). The valve was comprised of a plastic polycarbonate housing with a female Luer lock fitting at the proximal end and a distal tube outlet that was modified to receive the plunger diameter. The housing contained a duck-bill check valve fabricated from silicone elastomer.

A housing 7 mm long with a 1.5 mm outer diameter and a 0.35 mm inner diameter, was fabricated from polycarbonate tubing, with a sealing element disposed in the proximal end of the housing. The housing length was such that the distal tip of the housing extended 1.5 mm beyond the tip of the needle when assembled. A molded tissue interface and distal seal 3.5 mm long with an outer diameter of 1.9 mm and an inner diameter of 0.9 mm was fabricated from 50 Shore A durometer silicone. The tissue interface and distal seal was placed over the distal end of the housing. A housing compression spring of 0.08 N/mm spring force, an outer diameter of 1.5 mm and a wire diameter of 0.1 mm was placed over the needle to provide sealing force against the tissues. The housing compression spring had a free length of 4.8 mm and a compressed length of 0.8 mm. The spring was placed over the needle, then the housing and tissue interface and distal seal were placed over the needle and the spring was adhesively bonded to the proximal end of the housing at one end and the syringe barrel at the other end.

Example 12: Use of Fluid Delivery Device

A device according to Example 9 was used to deliver fluid to the suprachoroidal space in an eye. A human cadaver eye was prepared by placing it into a holding cup. An injection fluid was prepared by making up a solution of 0.01% fluorescein in phosphate buffered saline. The fluorescein solution was drawn up into a 1 ml syringe. The syringe was attached to the proximal Luer fitting of the device and 0.1 ml of the fluid was pushed into the reservoir of the device, which pushed the plunger proximally, compressing the plunger spring.

The device was aligned with the pars plana region of the cadaver eye and the tissue interface and distal seal was placed against the surface of the eye. The device was manually advanced along the axis and the needle penetrated through the distal seal and into the tissues of the eye. When the distal needle tip entered the suprachoroidal space of the eye, the fluid was rapidly expelled through the lumen of the needle under the force of the plunger compression spring without further manipulation of the injection device.

When all of the fluid was delivered, the device was removed from the eye. A scleral flap was made in the eye over the injection site. When the scleral flap was opened, fluoresceinated fluid was observed between the choroid and the sclera in the suprachoroidal space.

Example 13: Use of Fluid Delivery Device

A device according to Example 11 was used to deliver fluid to the suprachoroidal space in an eye. A porcine cadaver eye was prepared by placing it into a holding cup. An injection fluid was prepared by preparing a solution of 0.01% fluorescein in phosphate buffered saline. The fluorescein solution was drawn into a 1 ml syringe. The syringe was attached to the proximal Luer fitting of the device and 0.1 ml of the fluid was injected into the reservoir of the device, which pushed the plunger proximally, compressing the plunger spring.

The device was aligned with the pars plana region of the cadaver eye and the tissue interface and distal seal was placed against the surface of the eye. The device was manually advanced along the axis of the device and the needle penetrated through the distal seal and into the tissues of the eye. When the distal needle tip entered the suprachoroidal space of the eye, the fluid was rapidly expelled through the lumen of the needle under the force of the plunger compression spring without further manipulation of the injection device.

When all of the fluid was delivered, the device was removed from the eye. A scleral incision was made in the eye posterior to the injection site. When the incision depth reached the suprachoroidal space, fluoresceinated fluid was observed exiting the space.

The invention claimed is:

1. An injection device comprising:
   an elongated body with a proximal end and a distal end;
   a hollow needle with a proximal end and a distal end, the hollow needle comprising a shaft, wherein the distal end of the hollow needle comprises a distal tip and the proximal end of the hollow needle is fixed to the distal end of the elongated body;
   a reservoir for an injection material to be delivered through the hollow needle;
   a distal element comprising a proximal end and a distal end, wherein the distal element comprises a tissue interface and a distal seal, wherein the distal element is attached to the distal end of the hollow needle thereby sealing a needle lumen; and
   a plunger with a first force element providing an injection force to said injection material and the distal seal;
   wherein:
   the distal seal is configured to be penetrable by the distal end of the hollow needle by placement of the tissue interface on a tissue surface and manual advancement of the injection device;
   the distal element is configured to become slidable on the hollow needle to allow progressive increase in an effective length of the hollow needle and advancement of the hollow needle into tissue;
   the penetrated distal seal is configured to open a path for flow or delivery of the injection material from the distal end of the hollow needle; and
   the injection device is configured such that the injection force is applied to the injection material prior to penetration of the distal seal by the distal end of the hollow needle;
   wherein the injection material is injected automatically once the hollow needle reaches an appropriate location.

2. The injection device of claim 1 further comprising the injection material wherein the injection material is a flowable material and the tissue interface comprises a rubber or soft polymer to provide a seal of the needle lumen at the injection site and the distal element provides a liquid-tight seal around the shaft.

3. The injection device of claim 1 further comprising the injection material wherein the injection material is a solid or semi-solid, wherein the reservoir is within the needle lumen and the elongated body of the injection device.

4. The injection device of claim 1 wherein a flow path for filling the reservoir is provided from the reservoir through the plunger to a connector, a valve and/or a septum.

5. The injection device of claim 4 wherein the valve comprises a one-way valve to prevent flow out from the reservoir.

6. The injection device of claim 4 wherein the flow path is provided between the reservoir and a proximal connector wherein the valve in the flow path comprises a one-way check valve configured to allow filling of the reservoir with the injection material to pressurize the reservoir.

7. The injection device of claim 1 further comprising the injection material wherein the injection material is a solid or semi-solid.

8. The injection device of claim 1, wherein the plunger is within the needle lumen at the proximal end of the hollow needle and the reservoir is within the needle lumen.

9. The injection device of claim 8, wherein the hollow needle extends proximally in the elongated body of the injection device.

10. The injection device of claim 1 additionally comprising a second force element between the distal end of the elongated body of the injection device and the proximal end of the distal element configured to provide a forward directed force on the distal element and against the tissue surface by the distal element to maintain a seal on the tissue surface.

11. The injection device of claim 1 additionally comprising a collapsible element between the distal end of the elongated body of the injection device and the proximal end of the distal element configured to prevent distal movement of the distal element due to the injection force and configured to allow proximal travel of the distal element during advancement of the hollow needle into the tissue.

12. The injection device of claim 11 wherein the collapsible element comprises elongated struts.

13. The injection device of claim 11 wherein the collapsible element comprises nitinol.

14. The injection device of claim 1 additionally comprising a collapsible element between the distal end of the elongated body of the injection device and the proximal end of the distal element configured to provide a forward directed force on the distal element and against the tissue surface to maintain a seal on the tissue surface.

15. The injection device of claim 14 wherein the collapsible element is configured to travel proximally along a length of the hollow needle and to provide an initial force wherein the initial force is applied during a first 0.5 mm of travel of the distal element proximally along the hollow needle and the collapsible element is configured to provide a constant force during greater than 0.5 mm of travel of the distal element proximally along the hollow needle.

16. The injection device of claim 1 wherein the distal element further comprises a friction element configured to promote contact of the tissue interface with the tissue surface.

17. The injection device of claim 1 wherein the tissue interface and the distal seal are mounted on a tubular distal housing wherein the distal housing is configured to move proximally toward the elongated body when the hollow needle is inserted into the tissue surface.

18. The injection device of claim 17 additionally comprising an elastomeric element which is compressed between the housing and the hollow needle to seal the housing.

19. The injection device of claim 1 wherein the first force element and/or a second force element is a spring.

20. The injection device of claim 1 wherein the first force element is a spring which is mechanically coupled to the plunger.

21. The injection device of claim 1 wherein the first force element and/or a second force element is a pressurized gas.

22. The injection device of claim 1 wherein the distal element comprises a rubber or elastomer distal element.

23. The injection device of claim 1 wherein the distal element is elastically compressible.

24. The injection device of claim 1 wherein placement of the injection material in the injection device provides the injection force to the injection material.

25. The injection device of claim 1 wherein the elongated body comprises an exterior and an interior and the injection force is activated by a mechanism to compress the first force element from the exterior of the elongated device.

26. The injection device of claim 1 wherein the first force element is constrained prior to use and the injection force is activated by mechanically releasing the constrained first force element.

27. The injection device of claim 1 wherein the hollow needle has the effective length from 1 mm to 4 mm.

28. The injection device of claim 1 wherein the hollow needle has the effective length from 10 mm to 15 mm.

29. The injection device of claim 1 wherein the hollow needle has the effective length from 0.35 mm to 2 mm.

30. A method for treatment of an ocular disease or condition by injection of an injection material to a suprachoroidal space or a supraciliary space comprising filling the reservoir of the injection device of claim 1 with the injection material, whereby the filling compresses the first force element of the injection device to provide the injection force on the injection material, placing the tissue interface of said injection device on the tissue surface and manually advancing the hollow needle of said injection device through the distal seal to open the path for flow from the distal tip of the hollow needle, and advancing the hollow needle into the tissue until the injection material is automatically injected.

31. The method of claim 30 where the injection material comprises a steroid, non-steroidal anti-inflammatory agent, antibiotic, VEGF inhibitor, anti-TNF alpha agent, mTOR inhibitor, cell therapy, anti-hypertensive agent, antihistamine, aminosterol or neuroprotective agent.

32. The method of claim 30 wherein the ocular disease or condition comprises inflammation, infection, macular degeneration, retinal degeneration, neovascularization, proliferative vitreoretinopathy, glaucoma or edema.

33. A method for treatment of an ocular disease or condition by injection of an injection material to a suprachoroidal space or a supraciliary space comprising inserting a cartridge containing the injection material into the reservoir of the injection device of claim 1 activating the first force element of the injection device to provide the injection force on the injection material, placing the tissue interface of said injection device on the tissue surface and manually advancing the hollow needle of said injection device through the distal seal to open the path for flow of the injection material from the distal tip of the hollow needle, and advancing the hollow needle into the tissue until the injection material is automatically injected.

34. A method for treatment of an ocular disease or condition with the device of claim 1, wherein the injection material comprises a liquid or flowable injection material, wherein the treatment comprises delivery of the injection material to a suprachoroidal space or a supraciliary space comprising filling the injection device with the injection material, activating the first force element of said injection device to provide the injection force on the injection material, placing the tissue interface of the injection device on the tissue surface and manually advancing the hollow needle of the injection device through the distal seal to open the path for flow from the distal tip of the hollow needle, and advancing the hollow needle into the tissue until the injection material is automatically injected.

35. A method for treatment of an ocular disease or condition with the device of claim 1, wherein the injection material comprises a solid or semi-solid injection material, wherein the treatment comprises delivery of the injection material to a suprachoroidal space or a supraciliary space comprising filling the injection device with the injection material, activating the first force element of said injection device to provide the injection force on the injection material, placing the tissue interface of the injection device on the tissue surface and manually advancing the hollow needle of the device through the distal seal to open the path for flow of the injection material from the distal tip of the hollow needle, and advancing the hollow needle into the tissue until the injection material is automatically injected.

36. A method for injection of the injection material into a suprachoroidal space using the injection device of claim 1 comprising subjecting the injection material to the injection force by the first force element prior to introduction of the distal tip of the hollow needle into the tissue, advancing the hollow needle through the distal seal opening the path for flow of the injection material from the distal tip, thereby enabling single-handed use of the injection device without actuation of injection by a valve or trigger on the elongated body of the injection device.

37. A method for injection of injection material into a supraciliary space using the injection device of claim 1 comprising subjecting the injection material to the injection force by the first force element prior to introduction of the distal tip of the hollow needle into the tissue, advancing the hollow needle through the distal seal opening the path for flow of the injection material from the distal tip, thereby enabling single-handed use of the injection device without actuation of injection by a valve or trigger on the elongated body of the injection device.

38. The injection device of claim 1 wherein the distal seal is configured with a complementary bevel in a lumen of the distal element to provide close apposition to the distal seal of the needle bevel.

* * * * *

UNITED STATES PATENT AND TRADEMARK OFFICE
CERTIFICATE OF CORRECTION

PATENT NO. : 11,096,822 B2  
APPLICATION NO. : 15/512130  
DATED : August 24, 2021  
INVENTOR(S) : Ronald K. Yamamoto and Stanley R. Conston Page 1 of 1

It is certified that error appears in the above-identified patent and that said Letters Patent is hereby corrected as shown below:

In the Claims

At Column 25, Line 24, Claim 10, delete "a forward directed force".

At Column 25, Line 42, Claim 14, delete "a forward directed force".

Signed and Sealed this  
Twenty-third Day of November, 2021

Drew Hirshfeld  
*Performing the Functions and Duties of the*  
*Under Secretary of Commerce for Intellectual Property and*  
*Director of the United States Patent and Trademark Office*